United States Patent [19]

Pastan et al.

[11] Patent Number: 5,242,813
[45] Date of Patent: Sep. 7, 1993

[54] MOUSE MONOCLONAL ANTIBODIES SPECIFIC FOR NORMAL PRIMATE TISSUE, MALIGNANT HUMAN CULTURAL CELL LINES HUMAN TUMORS

[75] Inventors: Ira Pastan, Potomac; Mark C. Willingham, Bethesda, both of Md.

[73] Assignee: The United States of America as represented by the Department of Health and Human Services, Bethesda, Md.

[21] Appl. No.: 596,289

[22] Filed: Oct. 12, 1990

[51] Int. Cl.$^5$ .................. C12N 13/00; C12N 5/00; A61K 35/14
[52] U.S. Cl. ................. 435/70.21; 435/172.2; 435/240.1; 530/388.7; 530/388.8
[58] Field of Search ............. 435/70.21, 172.2, 240.1; 530/388.7, 388.73, 388.75, 388.8

[56] References Cited

FOREIGN PATENT DOCUMENTS 2020247 12/1990 Canada .

OTHER PUBLICATIONS

Pastan, et al *Cancer Research* 51:3781-3787 '91.
Abe, et al *JBL* 258(19): 11793-11797 '83.
Fine et al., *J. Invest. Dermatol.*, 92(16):825-830 (1989).
Hellstrom et al., *Cancer Res.*, 50:2183-22190 (1990).
Osborne et al., *J. Invest. Dermatol.*, 85:385-388 (1985).
Pastan et al., *Cell*, 47:641-648 (1986).
Hamilton et al., *Cancer Res.*, 43:5379-5389 (1983).
Bast et al., *J. Clin. Invest.*, 68:1331-1337 (1991).

*Primary Examiner*—David L. Lacey
*Assistant Examiner*—Donald E. Adams
*Attorney, Agent, or Firm*—Townsend and Townsend Khourie and Crew

[57] ABSTRACT

The subject invention relates to monoclonal antibodies and uses thereof. In particular, the invention relates to three monoclonal antibodies, referred to as B1, B3, and B5, which are useful in the treatment and diagnosis of many forms of cancer.

8 Claims, 1 Drawing Sheet

MOUSE MONOCLONAL ANTIBODIES SPECIFIC FOR NORMAL PRIMATE TISSUE, MALIGNANT HUMAN CULTURAL CELL LINES HUMAN TUMORS

BACKGROUND OF THE INVENTION

1. Technical Field

The subject invention relates to monoclonal antibodies and uses thereof.

In particular, the invention relates to three monoclonal antibodies, referred to as B1, B3 and B5, which are useful in the treatment and diagnosis of many forms of cancer.

2. Background Information

Current therapies for metastic human cancers, such as radiation or chemotherapy, center on agents that selectively kill rapidly growing cancer cells. Unfortunately, many tumors do not show an unusually fast growth rate compared to important normal tissues, such as bone marrow or the epithelium of the gastrointestinal tract. An alternative group of therapeutic approaches targets unique chemical structures on the surface of tumor cells for therapy, most often employing antibodies that bind selectively to these target molecules. One of these therapeutic approaches employs antibodies that are coupled to cell-killing agents, such as plant or bacterial toxins. These antibody-toxin complexes, immunotoxins, have been shown to be capable of selectively killing tumor cells in model tumor systems in tissue culture and in laboratory animals (Pastan, et al, *Cell*, 47:641–48 (1986)). In spite of many attempts to isolate such tumor-specific antibodies for human therapy, there are still very few antibodies identified that selectively bind only to tumor cells and not to other important normal tissues. Isolation of such tumor-specific antibodies is, therefore, of importance for the application of such immuno-directed therapies.

Monoclonal antibody methodology as originally described by Kohler and Milstein (*Nature* 156:495-97 (1975)) and disclosed in Koprowski, et al. (U.S. Pat. No. 4,172,124) has allowed the isolation of antibodies in pure form for the construction of therapeutic agents. However, two problems have prevented the application of many previously isolated antibodies. First, many monoclonal antibodies reactive with tumor cells also react with important normal human tissues. Secondly, many of the isolated antibodies bind to surface elements that do not efficiently mediate the entry of toxin conjugates into cells by endocytosis. The present invention includes three monoclonal antibodies, B1, B3, and B5, that selectively bind to some human tumors, but not to many important normal tissues. These antibody, when incorporated as the targeting element of an immunotoxin, also has been shown to allow efficient entry of these toxic agents into cells.

Previously, antibodies reactive with the Lewis Y antigen have been isolated and characterized. Recently, two antibodies, BR64 and BR96 have been described (Hellstrom et al., *Cancer Res.*, 50:2183-90 (1990)) that react with Lewis Y antigen, one of which (BR64) is not useful for immunotherapy because of its reactivity to capillaries in human cardiac muscle. BR96, however, shows reactivities that might make an immunotoxin constructed with this antibody potentially useful. The three new monoclonal antibodies, B1, B3, and B5, referred to above, which were isolated using a different cell type for immunizations and using morphologic screening methods, are similar, but not identical, to BR96. These differences in reactivity to tumors, normal tissues, and carbohydrate epitopes make these three new antibodies potentially useful for the therapy and diagnosis of some forms of human cancer.

SUMMARY OF THE INVENTION

The subject invention relates to three monoclonal antibodies, referred to as B1, B3 and B5, and to uses thereof.

B1, B3 and B5 exhibit a strong reactivity toward various mucin-producing, as well as non-mucin-producing primate carcinomas. Thus, these antibodies will be useful in the design of targeted therapeutic agents utilized in the diagnosis and treatment of human cancers.

In particular, the present invention relates to a hybridoma which produces a monoclonal antibody specific for a cell surface epitope wherein said epitope is characterized by expression on normal primate tissue, malignant human cultured cell lines and human tumors.

The present also includes a monoclonal antibody specific the cell surface epitope having the above properties. The class of said monoclonal antibody is IgG or IgM.

The malignant human cultured cell lines, referred to above, are selected from the group consisting of A431, MCF-7, HTB 20, and HTB 33. The normal primate tissue is derived from, for example, the esophagus, bladder or stomach. The human tumor noted above is derived from colon, gastric or ovarian carcinomas.

The present invention also relates to three separate hybridomas having the accession numbers ATCC HB 10569, HB 10572, and HB 10573, respectively.

The monoclonal antibody produced by the hybridoma of accession number ATCC HB 10572 is B1. The monoclonal antibody produced by the hybridoma of accession number ATCC HB 10573 is B3, and the monoclonal antibody produced by the hybridoma of accession number ATCC HB 10569 is B5.

Furthermore, the present invention also includes a method of treating cancer comprising administering to a patient, in need of said treatment, an amount of a conjugate of the monoclonal antibody sufficient to effect said treatment. The monoclonal antibody may be conjugated with, for example, a toxin, radionuclide or chemotherapeutic drug. The toxin may be, for instance, Pseudomonas exotoxin. The chemotherapeutic drug may be, for example, vinblastin or daunomycin.

The present invention also includes a method of diagnosing cancer in a patient comprising the steps of:

drawing a blood sample from said patient;

adding a monoclonal antibody to said sample in an amount sufficient to react with cancer shed antigen to form an antigen-antibody complex; and detecting whether cancer is present in said patient by measuring the presence or absence of said complex.

Furthermore, the present invention also includes a method of diagnosing cancer in a patient comprising the steps of removing a tissue or fluid sample from said patient;

adding the monoclonal antibody to the sample; and visualizing the presence of the antibody in the sample.

The present invention also includes a pharmaceutical composition comprising the monoclonal antibody in a concentration sufficient to inhibit tumor growth, together with a pharmaceutically acceptable carrier.

DETAILED DESCRIPTION OF THE INVENTION

Figure 1:
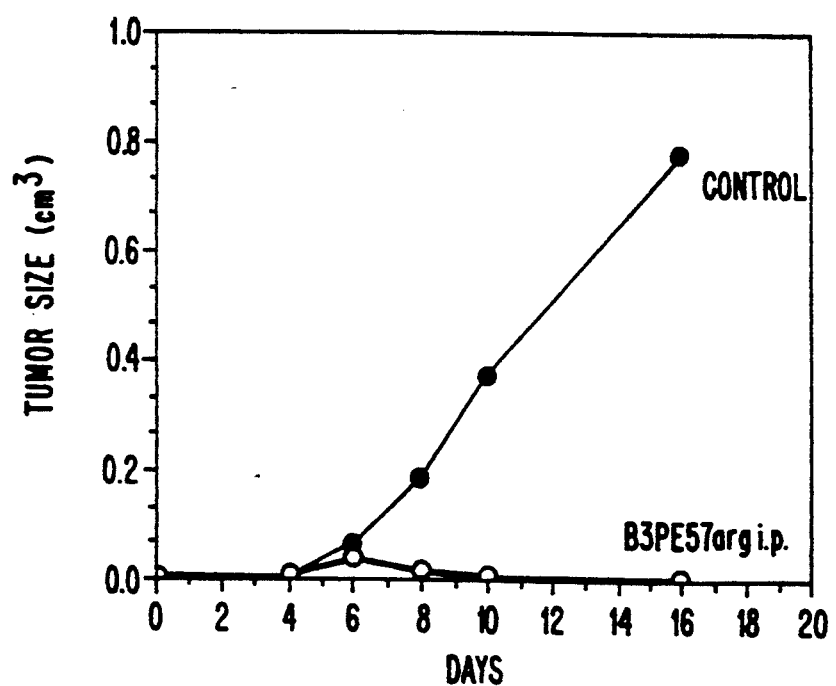
FIG. 1 represents the antitumor activity of BE-PE$^{Arg}$ 57 in mice. Nude mice (20 g) were injected with $3 \times 10^6$ cells subcutaneously on day 0. Treatment with 0.75 ug per dose was given I.P. on days 4, 6 and 8.

In order to produce the B1 and B3 monoclonal antibodies of the present invention, mice can be tolerized to normal human kidney membranes and immunized with MCF-7 cells (May et al., *American Type Culture Collection Catalog of Cell Lines and Hybridomas*, (May et al., ATCC 1988) 6th Ed. (1989), Matthew et al., *J. Immunol Methods* 100:73-82 (1987) and Willingham et al., *Proc. Natl Acad. Sci. USA* 84:2474-78 (1987)). In contrast, in order to produce the B5 monoclonal antibodies, mice are not tolerized and can be immunized with A431 cells (May et al., supra). Spleens from the immunized mice are then removed, and the suspended cells can be fused, for example, with AG8 mouse myeloma cells, using polyethylene glycol. Appropriate clones can be selected after screening procedures have been carried out. One screening procedure may involve selecting clones which react with human colon and gastric cancers and not with normal human liver, kidney or colon tissues. This selection process is important for isolating clones that react with tumors, rather than normal tissue, for the use of such antibodies in selective human immunotherapy of cancer.

After subcloning of such antibodies, the isotope of the clones can be determined. The present inventors have established that the isotope for the B1 and B3 clones is $IgG_{1k}$, whereas the isotope for the B5 clone is IgM. Antibody can be purified from the supernatant of the clones.

Once the antibodies are produced, their properties may then be characterized. For example, one may characterize precisely which primate tissue epitopes are reactive with the B1, B3 and B5 antibodies.

Reactivity is defined as detectable binding to the surface of living cells using immunohistochemical methods. Such a determination is necessary so that target agents may be designed which are toxic to tumors but not to important normal tissues.

The distribution of reactivity in normal human tissues, human tumors and normal cynomologous monkey tissues is summarized in Table I below.

TABLE I

Immunohistochemical Localization of B1, B3, B5, and BR96 in Normal Human and Monkey Tissues

| | B1 | B3 | B5 | BR96 |
|---|---|---|---|---|
| NORMAL HUMAN TISSUES | | | | |
| Liver | (−)(5/5) (+ large bile duct epith) | (−)(5/5) (+ large bile duct)(2/2) | (−)(1/1) | (−)(4/4) (+ large bile duct)(1/1) |
| Kidney | (−)(5/5) | (−)(5/5) | (+/− apic.tub(1/2) | (−)(3/4)(+ ap. d.tub)(1/4) |
| Cardiac Muscle | (−)(6/6) | (10/10) | (−)(6/6) | (−)(6/6) |
| Lung | (++ Type II pneum.)(1/2) | (+ Type II pneum.)(5/7) | (++ Type II pneum.)(1/1) | (−)(1/1) |
| Cerebal Cortex | (−)(2/2) | (−)(2/2) | (−)(3/3) | (−)(2/2) |
| Cerebellum | (−)(2/2) | (−)(2/2) | (−)(3/3) | (−)(2/2) |
| Spinal Cord | (−)(2/2) | (−)(2/2) | (−)(2/2) | (−)(2/2) |
| Pituitary | (−)(1/1) | (−)(1/1) | (−)(1/1) | nd |
| Bone Marrow | (−)(2/2) | (−)(1/1) | (−)(1/1) | (−)(1/1) |
| Adrenal | (−)(1/1) | (−)(1/1) | (−)(1/1) | (−)(3/3) |
| Spleen | (−)(1/1) | (−)(1/1) | nd | (−)(1/1) |
| Lymph Node | (−)(1/1) | (−)(1/1) | (−)(1/1) | nd |
| Skin | (−)(1/1) | (−)(2/2) | (−)(2/2) | (−)(3/3) |
| Skeletal Muscle | (−)(1/1) | (−)(1/1) | (−)(1/1) | (−)(2/2) |
| Peripheral Nerve | (−),?+ cap.endoth.(1/1) | (−)(?+ cap. endoth)(1/2) | (−)(2/2) | (?+ cap.endoth.)(1/1) |
| Tonsil | (+++ epith.)(2/2) | (++++ epith)(2/2) | (+++ epith.)(2/2) | nd |
| Esophagus | (+++ diff. epith.)(2/2) | (+++ diff. epith.)(2/2) | (+++ diff. epith)(1/1) | (+++ diff epith)(4/4) |
| Small Bowel | (+ mucin)(4/4) | (+ mucin)(3/3) | (+++ ap muc. gran.)(3/3) | (+++ muc.)(3/3) |
| Stomach | (++++ glnds, muc.)(3/3) | (++++ glnds, muc.)(3/3) | (+++ glnds, occ het)(3/3) | (++++ glnds, muc.)(4/4) |
| Normal Colon | (−)(7/7) | (weak het. epith)(6/6) | (++ het. muc.)(2/2) | (−;3/4)(het. +;1/4) |
| Bladder | (+++ epith.)(3/3) | (+++ epith)(3/3) | (+++ epith.)(3/3) | (+++ epith.)(3/3) |
| Pancreas | (#1 = het. + ac.; ducts; (#2 = + acini & ducts) | (+++ het, d & ac.)(2/2) | (+++ d & ac.)(1/1) | (+++ het ac. & muc.)(2/2) |
| Salivary Gland | (+ acini & ducts)(1/1) | (+++ d & ac.)(1/1) | (++++ ac. & d.)(1/1) | (+++ ac. & d.)(2/2) |
| Mammary Gland | (−)(1/1) | (het. + ducts)(1/1) | (+++ d, het glnds)(2/2) | (het. + ducts)(1/1) |
| Epididymis | (−)(1/1) | (−)(1/1) | (−)(1/1) | nd |
| Thyroid | (−)(1/1) | (+++ colloid, − epith)(1/1) | (−)(1/1) | (−)(1/1) |
| Parathyroid | (−)(1/1) | (−)(1/1) | (−)(1/1) | nd |
| Ovary | (−)(2/2) | (−)(1/1) | (−)(2/2) | nd |
| Fallopian Tube | (−)(1/1) | (−)(1/1) | (+/het)(1/1) | nd |
| Trachea | nd | (++++ epith.)(1/1) | nd | nd |
| Placenta | nd | (++++ fetal endoth.)(1/1) | nd | nd |
| NORMAL CYNOMOLOGOUS MONKEY TISSUES | | | | |

TABLE I-continued

Immunohistochemical Localization of B1, B3, B5, and BR96 in Normal Human and Monkey Tissues

| | B1 | B3 | B5 | BR96 |
|---|---|---|---|---|
| Liver | (−)(1/1) | (−)(1/1) | (−)(1/1) | (−)(1/1) |
| Kidney | (−)(occ. glom.)(1/1) | (+ ap dt, gl. caps.)(1/1) | (+ ap tub, gl. caps.)(1/1) | (−)(1/1) |
| Brain | (−)(2/2) | (−)(2/2) | (−)(1/1) | (−)(2/2) |
| Cerebellum | nd | nd | (−)(1/1) | nd |
| Spinal Cord | (−)(1/1) | (−)(1/1) | (−)(2/2) | (−)(1/1) |
| Periph. Nerve | nd | nd | (−)(1/1) | nd |
| Spleen | nd | nd | (−)(1/1) | nd |
| Lymph Node | nd | nd | (−)(1/1) | nd |
| Skin | (−)(1/1) | (−)(1/1) | (−, ex. + seb. glnds)(1/1) | nd |
| Skeletal Muscle | nd | nd | (−)(1/1) | nd |
| Esophagus | (+++ diff epith)(1/1) | (++ diff epith)(1/1) | (+++ diff epith)(1/1) | (+++ diff epith)(1/1) |
| Small Bowel | (−)(1/2)(+ muc gran)(1/2) | (−)(2/2) | (++ ap muc. B glnds)(1/1) | (−)(2/2) |
| Stomach | (het + glnds)(1/2) | (+++ glnds)(2/2) | (+++ glnds)(1/1) | (+++ glnds, het.)(1/1) |
| Colon | (−)(1/1) | (−)(1/1) | nd | (−)(1/1) |
| Bladder | (−)(1/1) | (+/−)(1/1) | (+++ epith)(1/1) | nd |
| Pancreas | (−; + muc)(2/2) | (−; + muc)(3/3) | (++ het ac.)(2/2) | (+/− het)(2/2) |
| Salivary Gland | (het +++ a & d)(2/2) | (++ het a; ++ d)(2/2) | (++ het a; ++ d)(3/3) | (++ het a; ++ d)(2/2) |
| Mammary Glands | (het +)(1/1) | (het. + g; ++ d)(1/1) | (het ++ g & d)(1/1) | nd |
| Thyroid | (−)(1/1) | (−)(1/1) | (−)(3/3) | (−)(1/1) |
| Para-thyroid | nd | nd | (−)(1/2)(het +)(1/2) | nd |
| Ovary | nd | nd | (−)(1/1) | nd |
| Vaginal Glands | nd | nd | (++++)(1/1) | nd |
| Uterine Cervix | (−)(1/1) | (−)(1/1) | (++ apic. muc.)(1/1) | nd |
| Uterine Endo-metrium | (−)(1/1) | (+ deep glands)(1/1) | (++ deep glands)(1/1) | nd |
| Thymus | (−)(1/1) | (−)(1/1) | (−)(1/1) | nd |
| Trachea | (−)(1/1) | (+ apic epith, het gl.)(1/1) | (+ apic epith & gl)(1/1) | nd |
| Tongue | (−)(1/1) | (+ diff. epith)(1/1) | (++ diff epith)(1/1) | nd |

Immunohistochemical analysis was performed on cryostat sections of fresh-frozen tissues, post-fixed in acetone and incubated with primary antibodies at 10 μg/ml except where indicated. Labeling was then performed using affinity-purified goat anti-mouse IgG conjugated to horseradish peroxidase, developed using diaminobenzidine, then treated with hematoxylin followed by osmium tetroxide.

(− = no localization; + = moderate; ++ = strong)(x/y = x examples of this pattern seen in y samples tested)(het = heterogeneous) nd = not determined.

As shown in Table I, the B1, B3 and B5-reactive epitopes are all found in varying amounts in the mucins of the stomach and small bowel, in the differentiated cell layer in the esophagus, in the epithelia of the tonsil, trachea and urinary bladder. These epitopes or antigens, which react with the B1, B3 and B5 monoclonal antibodies, can also be found in various other epithelia in a heterogeneous distribution, such as in the pancreas, salivary gland and mammary gland. B3 has the ability to react with the fetal endothelium, suggesting that the B3 monoclonal antibody represents an antigen expressed in fetal development.

Furthermore, as shown in Table I, the overall pattern of reactivity of the B1, B3 and B5 antibodies is different from the pattern of reactivity of a previously isolated antibody termed BR96 (Hellstrom et al., *Cancer Res.* 50:2183-90 (1990)). BR96 demonstrates some of the same reactivity patterns as observed with B1, B3 and B5. For example, BR96 reactivity is particularly notable in distal tubules in human kidney, as is B1 and B3 reactivity. However, there are distinct differences between these four antibodies in certain sites, such as in kidneys tubules, type II pneumocytes in the lung, mucin in the colon and in pancreatic ducts. For example, BR96 reactivity is not present in mucin in normal human colon sample, as is B5 reactivity. Such information can be significant in determining whether a monoclonal antibody administered for therapeutic purposes will be toxic with respect to normal tissues.

The above four antibodies can also be evaluated in normal monkey tissues (See Table I). Tissues similar to those in the human samples are reactive; however, similar to the human tissues, there are distinct differences between B1, B3, B5 and BR96 reactivity in kidney tubules, small bowel mucin, bladder epithelium, pancreas, cervical mucin, endometrial glands, and the epithelium of trachea and tongue. These differences indicate that each of these antibodies recognize different epitopes. Thus, the chemical structures of the epitopes are different.

Various cancer cell lines can also be examined for reactivity with B1, B3, B5 and BR96 using immunofluorescence. The results of such a study are shown in Table II presented below.

TABLE II

Immunofluorescence Localization of B1, B3, B5, and BR96 On Human Cultured Cell Lines

| CELL LINE | B1 | B3 | B5 | BR96 |
|---|---|---|---|---|
| A431 (epidermoid Ca) | +++ het | ++++ het | ++++ het | ++++ |
| MCF-7 (breast Ca) | ++++ | ++++ | ++++ | ++++ |
| OVCAR-3 (ovarian | − | − | ++++ het | ++++ |

TABLE II-continued

Immunofluorescence Localization of B1, B3, B5, and BR96 On Human Cultured Cell Lines

| CELL LINE | B1 | B3 | B5 | BR96 |
|---|---|---|---|---|
| Ca) | | | | |
| KB (cervical Ca) | − | +/− het | +++ het | − |
| HT-29 (colon Ca) | + | ++++ | +++ het | +/− |
| MDA-MB-468 (breast Ca) | ++++ | ++++ | nd | ++++ |
| DU145 (prostate Ca) | + het | ++ het | +++ het | ++++ |
| HTB20 (breast Ca) | +++ | +++ | +++ het | +++ |
| HTB33 (cervial Ca) | +++ | +++ het | +++ het | +++ |

Het = heterogeneous; (−) = negative; (+ = weakly positive; ++ = moderate; +++ = strong; ++++ = very strong). nd = not determined.

As clearly shown in Table II, B1, B3, B5 and BR96 react with some cell lines uniformly, However, there are differences in reactivity, especially for OVCAR-3, KB and HT-29 cells. Again such data suggests that the epitopes recognized by four antibodies are different from a structural standpoint. Furthermore, such differences in epitope structure and therefore in reactivity with monoclonals may be an advantage in therapy in some patients.

Tumors can also be examined for the expression of antigens which react with the 4 antibodies, using peroxidase immunohistochemistry. Table III (below) shows that the B1, B3, B5 and BR96 antibodies react well with carcinomas of colon and gastric origin, and mucinous ovarian carcinomas. Reactivity can be detected in a smaller number of breast, esophageal and other carcinomas.

acids, then extracted and the extracts immunoprecipitated, the reactive species of molecules that are precipitated by B1, B3 and B5 can be analyzed by gel electrophoresis and auto radiography. B1 aand B3 specifically immunoprecipitate protein bands of a very high molecular weight (>250,000 Daltons), consistent with their reactivity with high molecular weight mucins. Because B5 is an IgM antibody, for technical reasons this method is unable to show specifically reactive proteins.

Monoclonal antibodies B1, B3 and B5 can serve as targeting agents for the construction of immunotoxins, in which the monoclonal antibody is linked to a toxin, for example, Pseudomonas exotoxin (see Table IV below). As previously disclosed in Pastan, et al. (U.S. Pat. No. 4,545,985) conjugates of Pseudomonas exotoxin and monoclonal antibodies show efficacy in killing cells that are targeted by the epitope-reactive site of the antibodies. Constructions made by linking B1, B3 or B5 to such toxin would then be introduced into patients that had tumors that were reactive with these monoclonal antibodies, and the immunotoxins would bind to and kill the tumor cells within the patient. Normal tissues that were also reactive with these monoclonal antibodies would be affected if the antigenic sites were accessible to the blood circulation. In the case of many of the sites of expression of antigens reactive with B1, B3, and B5, the reactive epitope appears by immunohistochemistry to relatively inaccessible to the circulation, such as the reaction with mucins in the lumen of the gastrointestinal tract. Thus, it is not possible to predict with total certainty what the toxic effects of such immunotoxins would be in a human patient. Tumor cells that express these surface antigens, however, are rarely in a location that would render them inaccessible to the immunotoxin, and the tumor cells should therefore, be susceptible to targeted cell killing by immunotoxins constructed with B1, B3 or B5.

TABLE III

IMMUNOHISTOCHEMICAL REACTIVITIES OF HUMAN TUMORS WITH B1, B3, B5, and BR96

| | B1 | B3 | B5 | BR96 |
|---|---|---|---|---|
| Colon Ca | (++ het cells & mucin)(3/3) | (++++ cells & mucin)(9/12) (het ++)(3/12) | (+++ het)(3/3) | (+++)(3/3) |
| Gastric Ca | (++++ cells & mucin)(3/4) | (++++)(3/4) | (+++)(1/1) | (++++)(3/4) |
| Overian Ca | (mucinous = +++ cells & mucin) (1/1);(cystadenoCa = het +)(2/3) | (mucinous = ++++)(2/2) (cystadenoCa:(+++)(4/20) (het ++)(6/20) | (mucinous = +++)(1/1) (cystadenoCa:het +++) (2/2) | (+++ mucinous)(1/1) (+ het cystadenoCa) (1/2) |
| Breast Ca | (het +)(1/2) | (+++ het)(14/21) | (−)(2/2) | (+++)(5/7) |
| Esophageal Ca | nd | (het +)(4/9);(++++)(3/9) | nd | nd |
| Prostate Ca | nd | nd | (+++)(1/1) | (++ het)(2/2) |
| Cervical Ca | nd | (het +)(1/1) | (−)(1/1) | nd |
| Endometrial Ca | nd | (het ++)(1/1) | (++)(1/1) | nd |
| Lung Ca | nd | (het +)(1/3) | nd | nd |

Immunohistochemical analysis was performed on cryostat sections of fresh-frozen tissues, post-fixed in acetone and incubated with primary antibodies at 10 μg/ml except where indicated. Labeling was then performed using affinity-purified goat anti-mouse IgG conjugated to horseradish peroxidase, developed using diaminobenzidine, then treated with hematoxylin followed by osmium tetroxide.
(− = no localization; + = moderate; ++ strong)(x/y = x examples of this pattern seen in y samples tested) (het = heterogeneous) nd = not determined.

The results of Tables I, II and III indicate that B1, B3 and B5 react with many common tumors and appear to react with a limited number of normal tissue sites. In addition, these antibodies show distinct differences in reactivity in some varying tissue samples indicating that the precise epitopes they detect are different.

When MCF-7 cells bearing the B1, B3 and B5 epitopes are metabolically labelled using radioactive amino

TABLE IV

Activity of Immunotoxin Composed of B3 and a Pseudomonas Exotoxin Mutant in Which Lysine 57 is Converted to Arginine (B3-PE$^{Arg57}$)

| | ID$_{50}$ | |
|---|---|---|
| Cell Line | B3-PE$^{Arg57}$ ng/ml | MOPC-PE$^{Arg57}$ ng/ml |
| A431 Epidermoid Ca | 0.2 | >100 |

| TABLE IV-continued | | |
|---|---|---|
| MCF-7 Breast Ca | 0.3 | >100 |

$ID_{50}$ is the concentration of agent that inhibits protein synthesis by 50% in a 16 hour incubation.

In addition to bacterial or plant toxins conjugated to monoclonal antibodies, other effector agents may be used together with targeted monoclonal antibodies to treat or diagnose human cancer. For example, radionuclides conjugated to antibodies that bind to tumors can produce cell killing based on the high local concentration of radiation. Chemotherapeutic drugs, for example, vinblastine or daunomycin, can be coupled to antibodies and delivered at high concentration to cells that react with the antibodies. B1, B3, and B5 may provide a targeting mechanism for such combination of effector agents that could produce successful regression of reactive human tumors when introduced into patients.

In addition to the targeting of immunotoxins to tumors in a cancer patient, these antibodies also recognize materials such as surface mucins on tumor cells that would be expected to be shed into the surrounding tissues, picked up by the blood stream, and detectable in blood samples taken from distant sites. Such shed antigens have proven to be useful in the diagnosis of primary and recurrent cancers using antibodies that react to these shed antigens. A currently useful example of this is the CA125 antigen that can be assayed in sera from patients with ovarian cancer to predict recurrence or to confirm primary diagnosis of tumor. It is possible, therefore, that B1, B3 and B5 may be useful in the diagnosis of tumors.

Also, the selective reactivity of these antibodies with certain types of tumor cells could be exploited for anatomic pathological diagnosis of tumors, clarifying the type and origin of tumors, and whether a particular group of cells represents a recurrence of a previous tumor or the development of another primary tumor elsewhere. Such a diagnostic determination can be useful for the subsequent planning of anti-tumor therapy in each particular patient. In particular, immunohistochemical pathologic diagnosis in tissue sections (e.g., biopsies) or cytological preparations (e.g., Pap smears, effusions) can be performed using the monoclonal antibodies of the present invention.

Another potential use of such targeting antibodies could be in the diagnosis of macroscopic foci of tumor using antibodies B1, B3 or B5 coupled to radioisotopes that could be detected either by external body scanning (imaging diagnosis) or by localization using radiation detector probes at the time of exploratory surgery.

In addition to the initial clones of B1, B3 and B5 isolated as mouse monoclonal antibodies, variations of the constant regions of these antibodies incorporating constant regions of other species, such as human, could be performed, in which the resulting antibody would display less immunogenicity as a foreign antigen itself when introduced into a human patient. Pharmaceutical compositions can also be made using the monoclonal antibodies.

Also, the genes responsible for the variable regions of these antibodies could be isolated and targeting agents constructed using these variable region genes in tandem with genes for other proteins, such as toxin genes, or other effector proteins that could direct cell killing either directly or through the activation of endogenous mechanisms, such as the immune system. The variable regions of immunoglobulin genes encode the antigen binding site which enables the chimeric antibody toxin protein to bind to and kill target cells expressing the antigen reacting with antibodies B1, B3, and B5.

The present invention can be illustrated by the use of the following non-limiting examples.

EXAMPLE I

Production of the B1, B3 and B5 Monoclonal Antibodies

The human tumor cell lines OVCAR-3, KB, MCF-7, HT-29, MDA-MD-468, DU145, HTB20, and HTB33 have been previously described (Hay et al., *American Type Culture Collection Catalog of Cell Lines and Hybridomes*, 6th Ed. (1988)). For antibodies B1 and B3, mice were tolerized to normal human kidney membranes (Matthew et al., *J. Immunol. Methods* 100:73–82 (1978) and immunized with MCF-7 cells using methods previously described (Willingham et al., *Proc. Natl. Acad. Sci. USA* 84:2474–78 (1987)). For antibody B5, mice were not tolerized and were immunized with A431 cells. Spleens from immunized mice were removed and the suspended cells were fused with AG8 mouse myeloma cells. The resulting clones were screened two weeks later employing the ScreenFast (Life Technologies, Inc. Gaithersburg, Md.) large scale screening chamber using rhodamine indirect immunofluorescence on living MCF-7 and A431 cells for B1 or B3, and B5, respectively. Selected clones were secondarily screened using peroxidase immunohistochemistry on cryostat sections of human tumors and normal tissues. Clones B1, B3 and B5 were selected that reacted with human colon and gastric cancers, and not with normal human liver, kidney or colon. After sub-cloning, the isotypes of these clones was determined to be $IgG_{1k}$ for clones B1 and B3, and IgM for clone B5. Antibody was purified from the supernatants of these clones using serum-free defined culture media and ammonium sulfate precipitation.

EXAMPLE II

Determination of Distribution of Antigens Reactive with Antibodies B1, B3 and B5 In Human Tumor-Free Tissues, Human Tumors And Monkey Tissues Samples of normal human tissues, Cynomologous monkey tissues, and human tumors were fresh-frozen and cryostat sections were prepared for peroxidase immunohistochemistry as previously described (Willingham, FOCUS 12:62–67 1990)) using B1, B3 and B5 as primary antibodies. Localization of antibodies was detected by development of the peroxidase substrate reaction using diaminobenzidines. Tissues sections demonstrated major reactivies of B1, B3 and B5 in the epithelium of the tonsil, stomach, esophagus, and bladder, as well as in mucins of the small bowel and colon. Similar localization was found in monkey tissues in esophagus, small bowel, stomach, bladder, salivary gland, and pancreas with some differences being noted between the different antibodies (see Table I). Human tumors showed strong reactivity for B1, B3 and B5 in carcinomas of colon, stomach, ovary, and esophagus, with variable localization seen in carcinomas from breast, cervix, prostate, endometrium and lung (see Table III). All localizations, except as noted in Table I, represented antigen reaction that appeared to be on the surface of the cells, making these sites potential targets for immunotherapy.

EXAMPLE III

Determination of the Effectiveness of BE-PE As An Anti-Tumor Agent

B3 was coupled to Pseudomonas exotoxin as previously described (Willingham et al., *Proc. Natl. Acad. Sci. USA* 84:2474–78 (1987)). To do this, a mutant form of PE in which lysine 57 of PE was mutated to arginine ($PE^{Arg}57$) was used. The immunotoxin was purified and tested in tissue culture where it was shown to kill target A431 and MCF-7 cells (Table V). A control antibody (MOPC 21) was also coupled to $PE^{Arg}57$ and it had no cell killing activity. $B3-PE^{Arg}57$ was then given intraperitoneally to mice. The mice had been implanted with 3 million A431 cancer cells on day 0, and by day 4 had small cancers which were rapidly growing. The immunotoxin was given IP on days 4, 6, and 8 and, as shown in FIG. 1, the tumors regressed and apparently disappeared, whereas, in the control animals treated with diluent, the tumors grew rapidly.

We claim:

1. A hybridoma selected from the group consisting of HB10572, HB10573 and HB10569 which produces a monoclonal antibody specific for normal primate tissue, malignant human cultured cell lines and human tumors and which is not specific for normal human brain, liner or kidney tissue.

2. A monoclonal antibody selected from the group consisting of B1, B3 and B5, which are produced by the hybridomas of claim 1 and are specific for normal primate tissue, malignant human cultured cell lines and human tumors and which is not specific for normal human brain, liver or kidney tissue, and the class of said monoclonal antibody is IgG or IgM.

3. The hybridoma of claim 1 wherein said malignant human cultured cell lines are selected from the group consisting of A431, MCF-7, HTB 20, and HTB 33.

4. The monoclonal antibody of claim 2 wherein said malignant human cultured cell lines are selected from the group consisting of A431, MCF-7, HTB 20 and HTB 33.

5. The hybridoma of claim 1 wherein said normal primate tissue is derived from the group consisting of esophagus, bladder or stomach.

6. The monoclonal antibody of claim 2 wherein said normal primate tissue is derived from the group consisting of esophagus, bladder or stomach.

7. The hybridoma of claim 1 wherein said human tumor is derived from the group consisting of colon, gastric or ovarian carcinomas.

8. The monoclonal antibody of claim 2 wherein said tumor is derived from the group consisting of colon, gastric or ovarian carcinomas.

* * * * *

UNITED STATES PATENT AND TRADEMARK OFFICE
CERTIFICATE OF CORRECTION

PATENT NO. : 5,242,813
DATED : September 7, 1993
INVENTOR(S) : Pastan et al

It is certified that error appears in the above-indentified patent and that said Letters Patent is hereby corrected as shown below:

On the title page: Item [54] and Column 1, line 1, In the title, please delete "CULTURAL CELL LINES HUMAN TUMORS" and substitute therefore --CULTURED CELL LINES AND HUMAN TUMORS --.

Signed and Sealed this

Third Day of May, 1994

*Attest:*

BRUCE LEHMAN

*Attesting Officer*     *Commissioner of Patents and Trademarks*